(12) United States Patent
Gupta et al.

(10) Patent No.: US 10,905,374 B2
(45) Date of Patent: Feb. 2, 2021

(54) METHOD AND WEARABLE DEVICE FOR PERFORMING ACTIONS USING BODY SENSOR ARRAY

(71) Applicant: Samsung Electronics Co., Ltd., Suwon-si (KR)

(72) Inventors: Gaurav Gupta, Bangalore (IN); Sonu Agarwal, Bangalore (IN)

(73) Assignee: Samsung Electronics Co., Ltd., Suwon-si (KR)

( * ) Notice: Subject to any disclaimer, the term of this patent is extended or adjusted under 35 U.S.C. 154(b) by 328 days.

(21) Appl. No.: 15/989,747

(22) Filed: May 25, 2018

(65) Prior Publication Data

US 2018/0338720 A1  Nov. 29, 2018

(30) Foreign Application Priority Data

May 25, 2017 (IN) .............................. 201741018465
May 16, 2018 (IN) .............................. 201741018465

(51) Int. Cl.
*A61B 5/0488* (2006.01)
*A61B 5/053* (2006.01)
(Continued)

(52) U.S. Cl.
CPC .......... *A61B 5/6824* (2013.01); *A61B 5/0488* (2013.01); *A61B 5/1121* (2013.01);
(Continued)

(58) Field of Classification Search
CPC .......... G06F 3/017; G06F 3/015; G06F 3/014; G06F 1/163; A61B 5/0488; A61B 5/681; A61B 5/6824
See application file for complete search history.

(56) References Cited

U.S. PATENT DOCUMENTS

2012/0188158 A1  7/2012  Tan et al.
2013/0317648 A1  11/2013  Assad
(Continued)

FOREIGN PATENT DOCUMENTS

EP  3 104 259 A1  12/2016

OTHER PUBLICATIONS

Extended European Search Report dated Apr. 23, 2020, issued in a counterpart European application No. 18806395.2-1132 / 3622375.
(Continued)

*Primary Examiner* — Xuemei Zheng
(74) *Attorney, Agent, or Firm* — Jefferson IP Law, LLP

(57) ABSTRACT

A method for performing actions by a wearable device is provided. The method includes detecting at least one signal indicating a movement of a muscle of the wrist, via an array of biometric sensors exposed through an inner peripheral surface of a substantially circular band of the wearable device, identifying an orientation of the wearable device corresponding to the at least one signal, and providing, based at least in part on the identification, a function corresponding to the orientation of the wearable device. The method further includes detecting, by the wearable device, an absolute orientation of the wearable device using at least one of an inertial sensor and the one or more body sensors. The method further includes dynamically performing an action, by the wearable device, based on a pre-stored mapping of the at least one physiological parameter and the absolute orientation of the wearable device.

20 Claims, 15 Drawing Sheets

(51) Int. Cl.
- *G06F 3/01* (2006.01)
- *G06F 1/16* (2006.01)
- *A61B 5/00* (2006.01)
- *A61B 5/11* (2006.01)
- *G06N 20/00* (2019.01)

(52) U.S. Cl.
CPC ............ *A61B 5/681* (2013.01); *A61B 5/7475* (2013.01); *G06F 3/015* (2013.01); *G06F 3/017* (2013.01); *G06N 20/00* (2019.01)

(56) References Cited

U.S. PATENT DOCUMENTS

| | | | |
|---|---|---|---|
| 2014/0240103 A1 | 8/2014 | Lake et al. | |
| 2015/0084860 A1 | 3/2015 | Aleem et al. | |
| 2015/0289824 A1 | 10/2015 | Leininger et al. | |
| 2015/0301608 A1 | 10/2015 | Nagaraju et al. | |
| 2015/0370333 A1* | 12/2015 | Ataee | G06K 9/00335 345/156 |
| 2016/0313801 A1 | 10/2016 | Wagner et al. | |
| 2016/0349790 A1 | 12/2016 | Connor | |
| 2016/0370767 A1 | 12/2016 | Huang | |
| 2018/0360379 A1* | 12/2018 | Harrison | A61B 5/681 |

OTHER PUBLICATIONS

Zhang et al.; Advancing Hand Gesture Recognition with High Resolution Electrical Impedance Tomography; Oct. 19, 2016, Tokyo, Japan.
International Search Report dated Sep. 11, 2018, issued in the International Application No. PCT/KR2018/005964.
McIntosh, EMPress: Practical Hand Gesture Classification with Wrist-Mounted EMG and Pressure Sensing, 2016, San Jose, CA, USA.
Rekimoto, GestureWrist and GesturePad: UnobtrusiveWearable Interaction Devices, Interaction Laboratory Sony Computer Science Laboratories, Inc., http://www.csl.sony.co.jp/person/rekimoto.html, Tokyo, Japan.
Zhang, Tomo: Wearable, Low-Cost, Electrical Impedance Tomography for Hand Gesture Recognition, Pittsburgh, PA.
Indian Office Action dated Sep. 29, 2020, issued in Indian Application No. 201741018465.

* cited by examiner

METHOD AND WEARABLE DEVICE FOR PERFORMING ACTIONS USING BODY SENSOR ARRAY

CROSS-REFERENCE TO RELATED APPLICATION(S)

This application is based on and claims priority under 35 U.S.C. § 119(a) of an Indian Provisional patent application number 201741018465, filed on May 25, 2017, in the Indian Intellectual Property Office, and of an Indian Complete Specification patent application number 201741018465, filed on May 16, 2018, in the Indian Intellectual Property Office, the disclosure of each of which is incorporated by reference herein in its entirety.

1. FIELD

The disclosure relates to performing actions with a wearable device. More particularly, the disclosure relates to a method and system for orientation detection of the wearable device using a body sensor array for performing the actions.

2. DESCRIPTION OF RELATED ART

In recent times, there has been a great deal of focus on human machine interfaces, particularly in wearable devices and in applications relating to a virtual reality. Typically, the wearable device senses gestures that a user performs, while wearing the wearable device. The wearable device can be worn on the wrist or a forearm. Further the wearable device can sense orientation of the user's wrist or the forearm through inertial sensors. Further, the wearable device can sense muscle activity using electromyography (EMG) sensors.

Existing wearable devices are symmetric, that is, they do not have a fixed reference orientation. Existing wearable devices further require the user to have a specific alignment or a reference frame with respect to the wearable device on the wrist or forearm. Gesture detection with such wearable devices can have ambiguity depending on how the wearable device is oriented on the user's hand. In the wearable device, the orientation of a display might vary across users, and with time. For example, the wearable device may be turned (or rotated) around the arm or wrist. There remains a need for wearable device to detect gestures irrespective of whether the specific alignment or a reference frame is established.

The above information is presented as background information only to help the reader to understand the present invention. Applicants have made no determination and make no assertion as to whether any of the above might be applicable as prior art with regard to the present application.

SUMMARY

Aspects of the disclosure are to address at least the above-mentioned problems and/or disadvantages and to provide at least the advantages described below. Accordingly, an aspect of the disclosure is to provide a wearable device that includes a substantially circular band having an inner peripheral surface and an outer peripheral surface, an array of biometric sensors exposed through the inner peripheral surface, and at least one processor configured to detect at least one signal indicating a movement of a muscle of the wrist, via the array of the biometric sensors, identify an orientation of the wearable device corresponding to the at least one signal, and provide, based at least in part on the identification, a function corresponding to the orientation of the wearable device.

Another aspect of the disclosure is to provide a method for dynamically performing actions by a wearable device based on an orientation of the wearable device.

Another aspect of the disclosure is to provide a method and system for orientation detection of the wearable device using a body sensor array.

Another aspect of the disclosure is to provide a method for usage of the body sensor array along with a machine learning approach to determine the orientation of the wearable device on the user arm.

Another aspect of the disclosure is to provide a method for determination of absolute orientation using the body sensor array and inertial sensors.

Another aspect of the disclosure is to provide a method that identifies motion gestures based on the determined absolute orientation of the wearable device.

Additional aspects will be set forth in part in the description which follows and, in part, will be apparent from the description, or may be learned by practice of the presented embodiments.

In accordance with an aspect of the disclosure, a wearable device capable of being worn on a wrist of a user is provided. The wearable device includes a substantially circular band having an inner peripheral surface and an outer peripheral surface, an array of biometric sensors exposed through the inner peripheral surface, and at least one processor configured to detect at least one signal indicating a movement of a muscle of the wrist, via the array of the biometric sensors, identify an orientation of the wearable device corresponding to the at least one signal, and provide, based at least in part on the identification, a function corresponding to the orientation of the wearable device.

In an embodiment, the plurality of body sensors are configured to measure at least one physiological parameter by detecting at least one signal indicative of limb movement in response to the user performing a gesture and measuring at least one physiological parameter indicative of the limb movement from the at least one detected signal by mapping the limb movement in conjunction with the relative position of each of the plurality of body sensors.

In an embodiment, the orientation calibrator is configured to determine an orientation of the wearable band based on the measured physiological parameters by detect an absolute orientation of the wearable device using at least one of an inertial sensor or the plurality of body sensors and dynamically perform an action based on a pre-stored mapping of the at least one physiological parameter and the absolute orientation of the wearable device.

In an embodiment, the at least one physiological parameter is represented as one or more images indicative of an impedance map.

In an embodiment, the at least one physiological parameter is indicative of at least one of muscle activity of the user, finger movement performed by the user, the user's wrist contour, a force applied through a gesture by the user, a force applied on the wearable device by the user, a pulse rate of the user, an electrical activity produced by muscles of the user, changes in volume of an artery or a vein of the user or a cross-sectional impedance across the one or more body sensors.

In an embodiment, the orientation calibrator is further configured to detect a change in the at least one signal using at least one of an inertial sensor and plurality of body sensors, modify the at least one physiological parameter based on the change in the at least one signal, determine the absolute orientation of the wearable device based on the mapping and the at least one modified physiological parameter or dynamically perform an action based on the determined absolute orientation.

In accordance with another aspect of the disclosure, a method for performing actions by a wearable device capable of being worn on a wrist of a user is provided. The method includes detecting at least one signal indicating a movement of a muscle of the wrist, via an array of biometric sensors exposed through an inner peripheral surface of a substantially circular band of the wearable device, identifying an orientation of the wearable device corresponding to the at least one signal, and providing, based at least in part on the identification, a function corresponding to the orientation of the wearable device.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

Figure 1A:
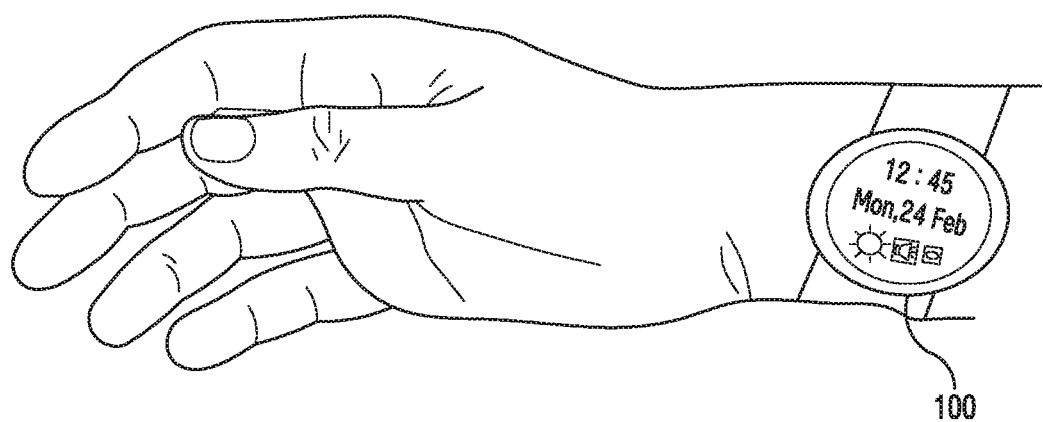
FIG. 1A illustrates a wearable device worn on a user's wrist for performing actions based on a detected orientation, according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Also, the various embodiments described herein are not necessarily mutually exclusive, as some embodiments can be combined with one or more other embodiments to form new embodiments. Herein, the term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein. Accordingly, the examples should not be construed as limiting the scope of the embodiments herein. Further it should be possible to combine the flows specified in different figures to derive a new flow.

As is traditional in the field, embodiments may be described and illustrated in terms of blocks which carry out a described function or functions. These blocks, which may be referred to herein as managers, engines, controllers, units or modules or the like, are physically implemented by analog and/or digital circuits such as logic gates, integrated circuits, microprocessors, microcontrollers, memory circuits, passive electronic components, active electronic components, optical components, hardwired circuits and the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the disclosure. Likewise, the blocks of the embodiments may be physically combined into more complex blocks without departing from the scope of the disclosure.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein.

Accordingly, embodiments disclosed herein provide a method for performing actions by a wearable device. Specifically, the embodiments disclosed herein provide a method for detecting the degree of rotation of the wearable device on the user's wrist. Based on the detection, the wearable device can detect an accurate motion or gesture of user's hand in consideration of the degree of rotation of the wearable device. The method includes measuring, by the wearable device, at least one physiological parameter from at least one signal detected using one or more body sensors. The method further includes detecting, by the wearable device, an absolute orientation of the wearable device using at least one of an inertial sensor and the one or more body sensors. The method further includes dynamically performing an action, by the wearable device, based on a pre-stored mapping of the at least one physiological parameter and the absolute orientation of the wearable device.

Referring now to the drawings and more particularly to FIGS. 1A through 10, where similar reference characters denote corresponding features consistently throughout the figure, there are shown preferred embodiments.

FIG. 1A illustrates a wearable device worn on a user's wrist for performing actions based on a detected orientation, according to an embodiment of the disclosure.

Referring to FIG. 1A, the wearable device 100 can be placed over a wrist or a forearm of the user. In some embodiments, the wearable device 100 can be placed over any other limb that may be convenient for the user. In some embodiments, the wearable device 100 can be a band worn on the user's wrist. In other embodiments, the wearable device 100 can be a bangle type device having an all around display. The wearable device 100 can be used to detect and respond to gestures made by the user. Gestures are typically categorized into dynamic and static gestures. A static gesture is a particular limb configuration and a pose. For example, pointing a finger forward or first grasping is a static gesture. A dynamic gesture is a moving gesture. For example, waving a hand is a dynamic gesture.

In some embodiments, the wearable device includes a substantially circular band body having an inner peripheral surface and an outer peripheral surface. In other embodiments, the wearable device 100 can be a band worn around a wrist of the user. For example, a display may be disposed on most of the outer surface of the bangle (or band) type wearable device 100 (not shown). Further, the wearable device 100 includes an array of surface electrodes or an array of body sensors (or biometric sensors) such as but not limited to, electromyography (EMG) sensors, force sensing resistor (FSR), photoplethysmogram (PPG), electrical impedance tomography (EIT), capacitance and the like, provided at the inner peripheral surface. In some embodiments, the body sensors are in close proximity to the user's skin to measure at least one physiological parameter of the user's body. In an embodiment, a plurality of body sensors can be disposed on the inner peripheral surface, configured to detect at least one signal indicative of limb movement.

The orientation of the wearable device is determined based on the measured physiological parameters. The orientation of the wearable device may indicate at least the degree of rotation (or the degree to which the wearable device worn on the user's wrist is rotated). For example, the orientation of the wearable device may indicate which direction (or orientation) the wearable device is worn on the user's wrist. When a user performs a static gesture, the array of body sensors measures corresponding changes in muscle configuration which is represented as image or data. For each orientation of the wearable device 100, a set of images are captured using the array of body sensors. In some embodiments, the image is indicative of cross-sectional impedance across the array of body sensors. The cross-sectional impedance changes corresponding changes in muscle configuration when there is muscle movement or finger movement. A machine learning model is generated using the images as a function of the orientation of the wearable device.

When the user performs the same static gesture, the machine learning model predicts the orientation of the wearable device based on the mapping between the image and the orientation.

In some embodiments, the wearable device 100 further includes inertial sensors. When the user performs a dynamic gesture, the continuous movement pertaining to the dynamic gesture is detected by the inertial sensors. Orientations pertaining to dynamic gestures can be the same if only inertial sensor data is considered. For example, a dynamic gesture pertaining to a horizontal movement of the arm and a dynamic gesture pertaining to a vertical movement of the arm can correspond to the same orientation. To remove this ambiguity, the orientation of the wearable device 100 predicted from the machine learning model is considered. The orientation is compensated from the orientation detected by the inertial sensors. Accordingly, the wearable device 100 detects different gestures using orientations detected by the array of body sensors and the inertial sensors.

Figure 1B:
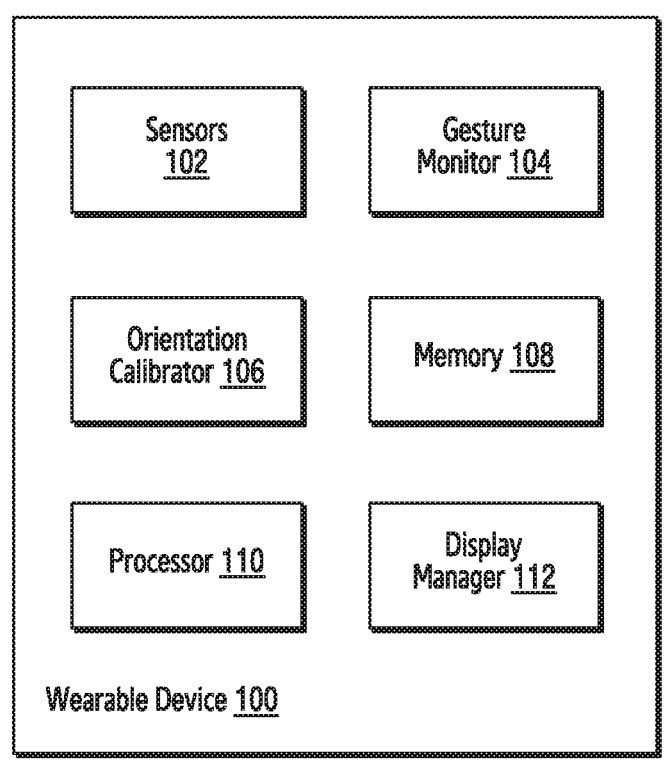
FIG. 1B is a block diagram illustrating various components of the wearable device, according to an embodiment of the disclosure.

FIG. 1B is a block diagram illustrating various hardware components of the wearable device 100 according to an embodiment of the disclosure.

Referring to FIG. 1B, the wearable device 100 includes sensors 102, a gesture monitor 104, an orientation calibrator 106, a memory 108, a processor 110 and a display manager 112.

The sensors 102 can be an array of sensors that include but are not limited to inertial sensors, EMG sensors, PPG sensors, FSR sensors and the like. The sensors 102 generate electrical signals that are indicative of any or a combination of a muscle activity under the user's skin in contact with the wearable device 102, the user's wrist contour, a force applied through a gesture made by the user with limb to which the wearable device 100 is attached and a pulse rate of the user. The sensors 102 can include an array of surface electrodes around the wrist of the user, each of the array of surface electrodes measuring an electrical signal when the user performs the gesture. An electrical impedance across the array of surface electrodes is measured when the user performs the gesture and the measured electrical impedance is represented as an image. The measured electrical impedance is directly proportional to a physiological parameter of the user's body. For example, an activity indicative of finger movement is detected as the electrical signal by the sensors 102. A change in electrical impedance across the sensors 102 results from the gesture being performed. Accordingly, the image indicative of the resultant electrical impedance is representative of the physiological parameter pertaining to the activity indicative of finger movement. For each orientation of the wearable device 100 on the wrist of the user as shown in FIG. 1A, an image is captured by the sensors 102.

In some embodiments, the sensors 102 include inertial sensors such as accelerometer, gyroscope or the like that measure the orientation of the wearable device 102.

The gesture monitor 104 and the orientation calibrator 106 can be any processing unit or a chipset that receives an input from the user through the sensors 102.

The gesture monitor 104 is a set of integrated chips that analyzes the images captured by the sensors 102 to sense a movement of a muscle of the user's arm and/or to identify finger movement performed by the user by analyzing the arm muscle movement in conjunction with the relative position of each of the sensors 102.

The orientation calibrator 106 is a set of chips disposed within the wearable device 100 that is communicably coupled to the sensors 102, the gesture monitor 104, the memory 108, the processor 110 and the display manager 112. The orientation calibrator 106 detects the electrical signals generated by the sensors 102 in response to the user performing a gesture. The orientation calibrator 106 measures the physiological parameter represented by the image based on the user gesture and the resultant information analyzed by the gesture monitor 104. A set of mappings between an orientation measured by the inertial sensors, the measured physiological parameters and an action to be performed as result of the identified gesture, is stored in the memory 108. The orientation calibrator 106 dynamically performs an action based on the mapping stored in the memory 108. The orientation calibrator 106 further modifies the physiological parameter based on any change in the physiological parameter due to a change detected in the electrical signal generated by the sensors 102. The absolute orientation of the wearable device 100 is determined by the orientation calibrator 106 based on the stored mapping and the modified physiological parameter, and accordingly the orientation calibrator 106 causes the wearable device 100 to dynamically perform the action based on the determined orientation.

The memory 108 includes storage locations to be addressable through the processor 110, the gesture monitor 104 and the orientation calibrator 106. The memory 108 is not limited to a volatile memory and/or a non-volatile memory. Further, the memory 108 can include one or more computer-readable storage media. The memory 108 can include non-volatile storage elements. For example non-volatile storage elements can include magnetic hard discs, optical discs, floppy discs, flash memories, or forms of electrically programmable memories (EPROM) or electrically erasable and programmable (EEPROM) memories. The memory 108 stores an orientation model, shown in FIG. 1C.

The processor 110 can be, but not restricted to, a central processing unit (CPU), a microprocessor, or a microcontroller. The processor 110 is coupled to the sensors 102, the memory 108, the gesture monitor 104, the orientation calibrator 106 and the display manager 112. The processor 110 executes sets of instructions stored on the memory 108.

The display manager 112 causes content to be displayed on a display screen on the wearable device 100. For example, the display manager 112 can cause status messages pertaining to whether a gesture is identified by the orientation calibrator 106 or if the wearable device 100 is powered on the display screen. At least some of the operations performed by the gesture monitor 104, the orientation calibrator 106, and/or the display manager 112 may be performed by the processor 110. For example, at least some part of the gesture monitor 104, the orientation calibrator 106, and/or the display manager 112 may be included in the processor 110.

Figure 1C:
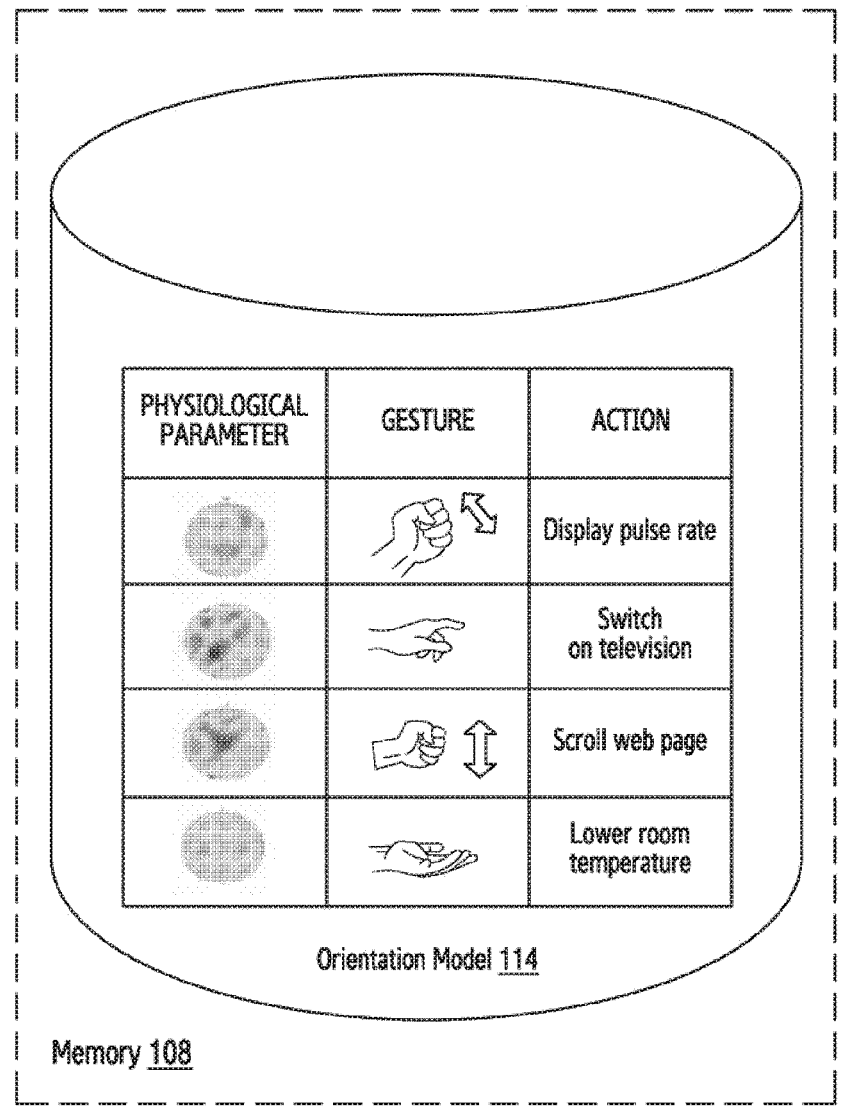
FIG. 1C is an example of an orientation model for performing actions based on the detected orientation, according to an embodiment of the disclosure.

FIG. 1C is an example of the orientation model 114 for performing actions based on the detected orientation, according to an embodiment of the disclosure.

Referring to FIG. 1C, the orientation model 114 may be stored in the memory 108 and may be dynamically updated based on the gestures performed with the wearable device 100 by the user. The physiological parameter measured by the orientation calibrator 106 is mapped to the orientation of the wearable device 100 and accordingly the action to be performed in response to the gesture of the wearable device 100 is determined. Specifically, the wearable device 100 can determine the accurate gesture by considering the detected orientation of the wearable device 100 when determining the gesture. The wearable device 100 performs the identified action upon successfully mapping the measured physiological parameter with the orientation. If no mapping is made, the orientation model 114 is updated with a new mapping of the measured physiological parameter with an absolute orientation detected by the inertial sensors or the sensors 102.

For example, as shown in the orientation model 114, the wearable device 100 displays a pulse rate of the user when user performs a gesture equivalent to moving the first horizontally. When the physiological parameter is measured and mapped to the shown absolute orientation, the corresponding action is performed. When the gesture is changed to a finger pointing forward, as shown in the second row in FIG. 1C, there may be no mapping available. Accordingly, the orientation calibrator 106 is tasked with linking an action as per a customization provided by the user. In the current example, the action could be to switch on a television (TV).

In some embodiments, the wearable device 100 can include hardware components such as communication unit, through which the wearable device can communicate with external devices in a network. The network can include a data network such as, but not restricted to, the Internet, local area network (LAN), wide area network (WAN), metropolitan area network (MAN) etc. In certain embodiments, the communication network can include a wireless network, such as, but not restricted to, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS) etc. Accordingly, the wearable device 100 is included with communication components facilitating communications over the communication network. In some embodiments, the wearable device 100 can be part of an internet of things (IoT) network. The wearable device 100 can control various nodes such as a thermostat, faucets, electrical appliances, phones etc. on the IoT network. For example, based on the user gesture, the wearable device 100 can direct the thermostat to lower temperature in a room.

Figure 2:
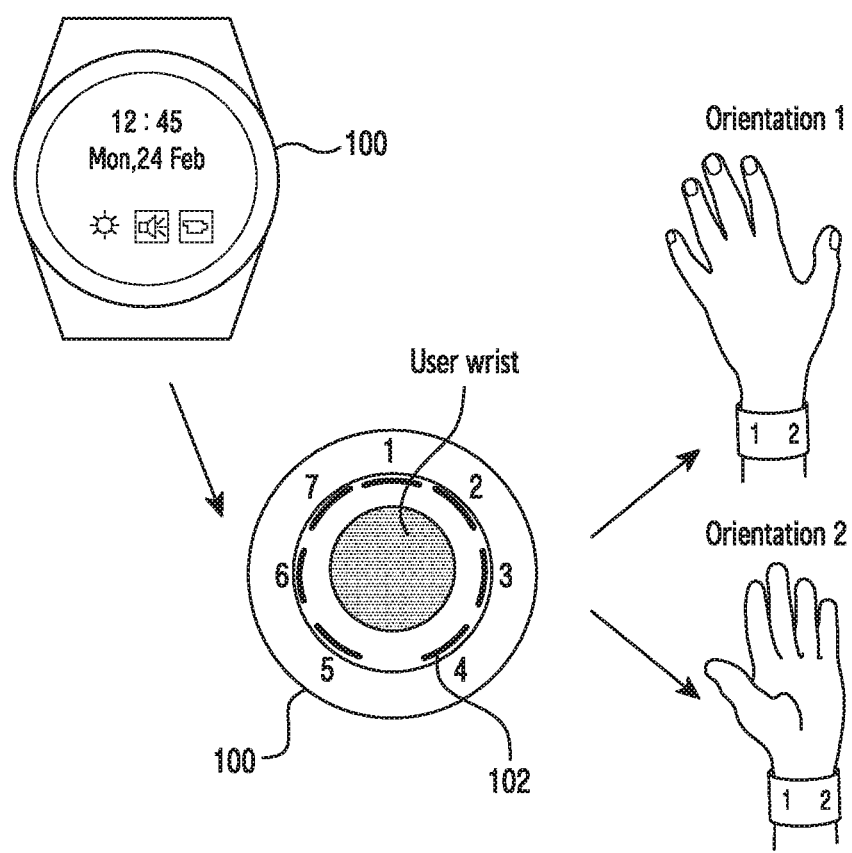
FIG. 2 illustrates an array of body sensors in the wearable device, according to an embodiment of the disclosure.

FIG. 2 illustrates an array of body sensors in the wearable device, according to an embodiment of the disclosure.

Referring to FIG. 2, the array or body sensors may correspond to the sensors 102. The sensors 102 may be the array of surface electrodes in the wearable device 100, according to an embodiment. Referring to FIG. 2, the sensors 102 may be disposed at the inner peripheral surface of the wearable device 100, for example, as a plurality of (e.g., seven in FIG. 2) sensors or electrodes. The sensors 102 measure the signals that are unique to the orientation of the wearable device 100 on the wrist/arm. The wearable device 100 can, by using the orientation model 114 (e.g., a machine learning based model), detect the absolute orientation of the wearable device 100 when worn in a new orientation based on the sensor measurement. Orientation 1 and 2 shown in FIG. 2 can be differentiated by the wearable device 100. The wearable device can identify whether the wearable device 100 is worn as Orientation 1 or worn as Orientation 2.

Figure 3A:
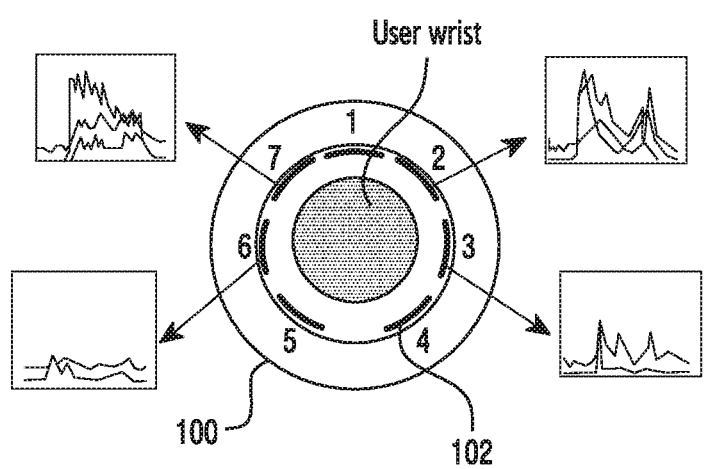
FIGS. 3A and 3B illustrate the array of body sensors and inertial sensors which can be used to detect the orientation of the wearable device, according to various embodiments of the disclosure.
Figure 3B:
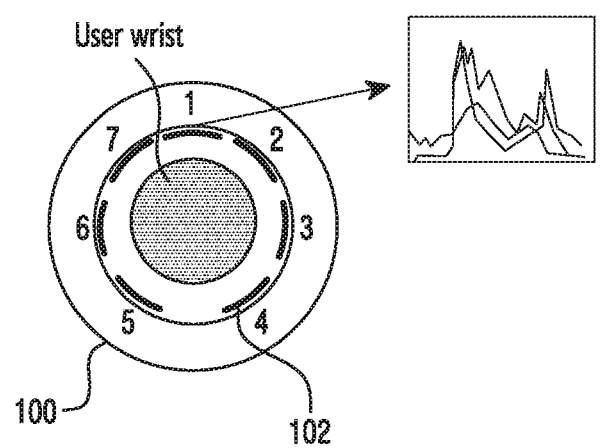

FIGS. 3A and 3B illustrate the sensors 102 which can be used to detect the orientation of the wearable device 100 on the user's arm/wrist according to various embodiments of the disclosure.

Referring to FIGS. 3A and 3B, the sensors 102 include an array of surface electrodes or sensors around the wrist, each measures a signal when a user performs a gesture as shown in FIG. 3A.

The other alternative being an array of surface electrodes or sensors around the wrist, but only one or at most two of them measure a signal. This might not necessarily require the user to perform a gesture and examples of sensors are PPG sensors or near infrared (NIR) sensors can be used to detect human body signals like a pulse rate from the top of the wrist, as shown in the FIG. 3B.

Figure 4:
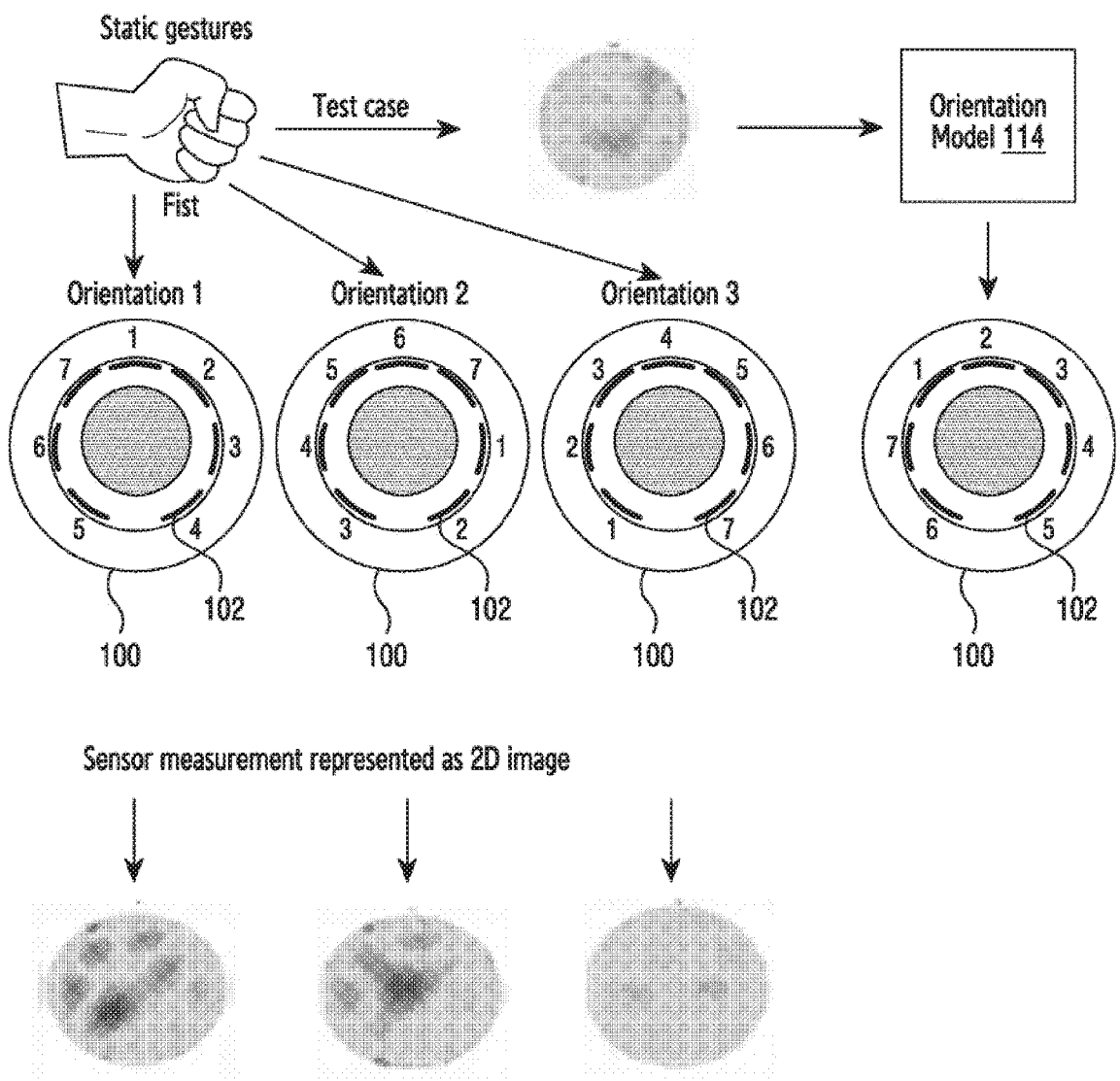
FIG. 4 illustrates the array of body sensors that capture sensor images for different orientations of the wearable device, according to an embodiment of the disclosure.
Figure 5:
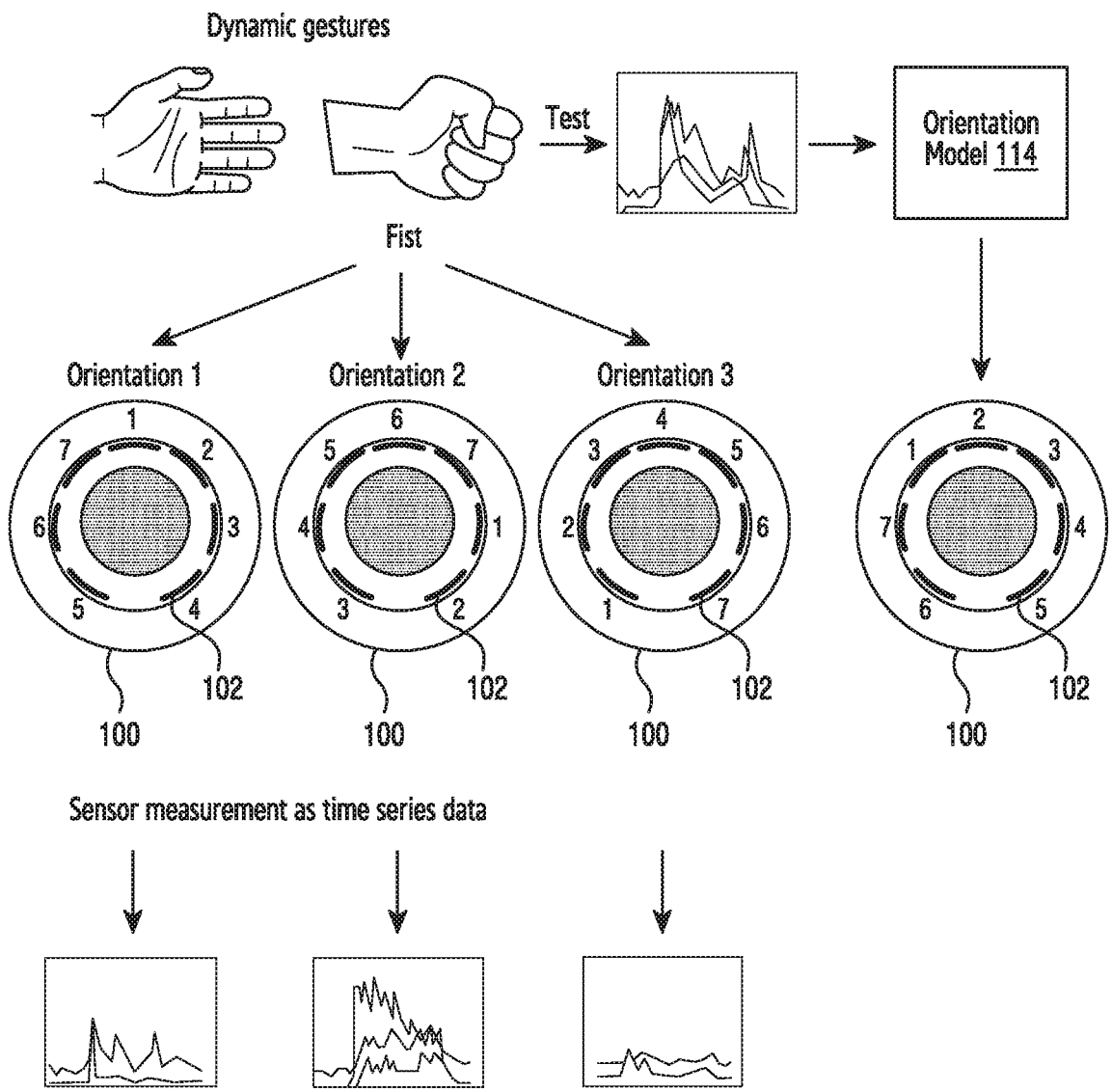
FIG. 5 illustrates the array of body sensors that use electrical impedance measurement and electromyography (EMG)/force sensing resistor (FSR), according to an embodiment of the disclosure.

FIGS. 4 and 5 illustrate the sensors 102 that use electrical impedance measurement and EMG/FSR according to various embodiments of the disclosure.

Referring to FIGS. 4 and 5, when the user performs a static gesture, as shown in FIG. 4, the sensors 102 measure the change in muscle configuration and is represented as an image. A set of sensor images are captured by the orientation calibrator 106 for different orientations of the wearable device 100 on the arm/wrist. As shown in FIGS. 4 and 5, the seven sensors 102 are shown at different placements in accordance with orientation 1, orientation 2 and orientation 3. The orientation model 114 is built using these images as a function of the orientation of the wearable device 100. For example, the orientation model 114 may be a machine learning model.

For a new orientation (shown as a test case in FIG. 4), the user first performs the same static gesture (or a designated gesture). The orientation calibrator 106 dynamically predicts the orientation of the wearable device 100 based on the corresponding image and the orientation model 114. Deep learning or machine learning techniques are used to update the orientation model 114 to associate the sensor signal to an orientation on the arm/wrist. The machine learning techniques can be but not limited to neural networks, pattern matching techniques for time series data like dynamic time warping (DTW), hidden Markov models using the generated images, deep neural network models using the generated images and the like. The orientation model 114 is trained using signal features from the EMG or FSR sensor. The wearable device 100 can estimate or identify the new orientation (shown as the test case in FIG. 4) based on the image corresponding to the new orientation and the orientation model 114 which is built using the images corresponding to the orientation 1, orientation 2, and orientation 3.

FIG. 5 shows a similar process as shown in FIG. 4 for a dynamic gesture. The signals detected by the orientation calibrator 106 can be time-based when the gesture is dynamic. Referring to FIG. 5, When the user performs a dynamic gesture, the sensors 102 (e.g., EMG or FSR) may detect time series data corresponding to each of the orientation 1, orientation 2, and orientation 3. A machine learning model (e.g., orientation model 114) may be trained using the signal features (or the time series data) from the EMR or FSR sensor. For a new test orientation, the wearable device 100 can predict the orientation of the wearable device 100, by using the model, based on the new time series data corresponding to the new text orientation and the model.

Figure 6:
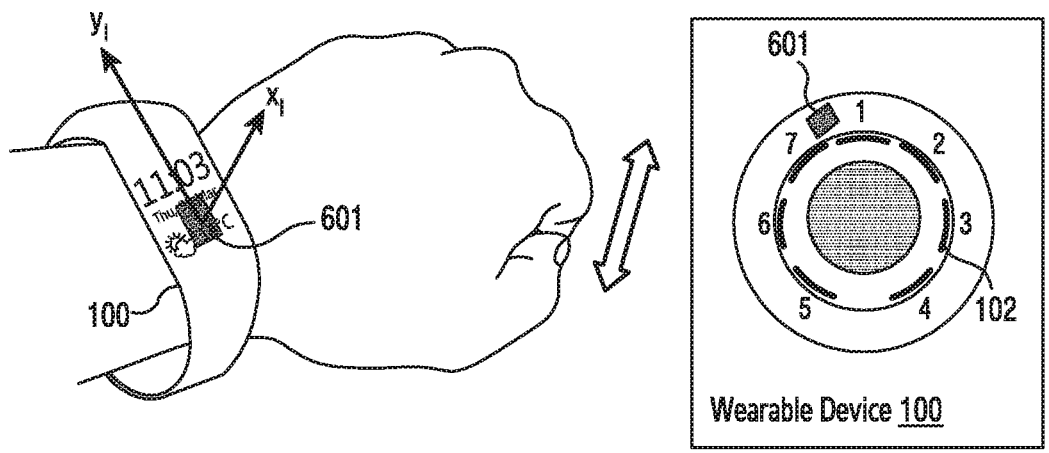
FIG. 6 illustrates various orientations of the wearable device for accurate gesture recognition, according to an embodiment of the disclosure.
Figure 6:
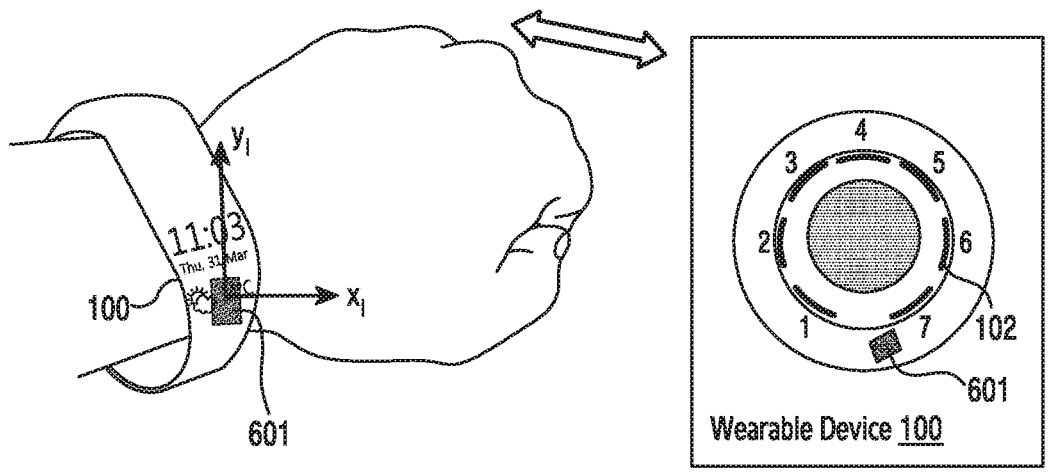

FIG. 6 illustrates various orientations for accurate gesture recognition by the wearable device 100 according to an embodiment of the disclosure.

Referring to FIG. 6, arm motion based gestures are detected by the inertial sensor in the wearable. In FIG. 6, the two orientations of the wearable device 100 record the same sensor measurement (rotation about y axis or parallel to x axis) for two different gestures. That is, if the wearable device 100 is rotated on the user's wrist (or the orientation of the wearable device 100 changes), the inertial sensor 601 may be difficult to distinguish between the horizontal motion and the vertical motion of the hand. This can be addressed if the absolute orientation of the wearable device 100 is known. The absolute orientation of the wearable device 100 is compensated for from the inertial sensor orientation which removes the ambiguity in gesture recognition. The wearable device 100 can identify an accurate gesture or motion of the hand based on the value (or data, signal) detected using the inertial sensor 601 and the sensors 102.

Figure 7:
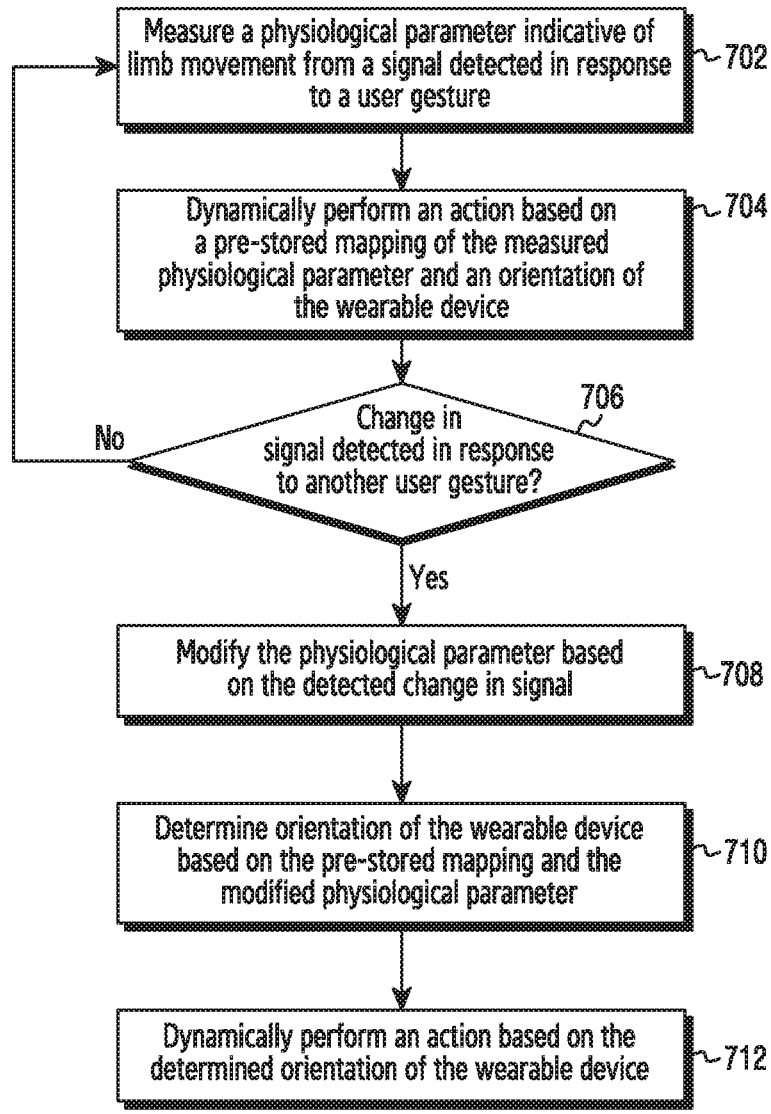
FIG. 7 is a flow diagram illustrating a method of performing actions by the wearable device, according to an embodiment of the disclosure.

FIG. 7 is a flow diagram that illustrates the method for performing actions by the wearable device 100 according to an embodiment of the disclosure.

Referring to FIG. 7, at operation 702, the orientation calibrator 106 measures the physiological parameter indicative of limb movement from the signal generated by the sensors 102 in response to the user performing a gesture. The physiological parameter is represented by the image based on the user gesture and the resultant information analyzed by the gesture monitor 104. A set of mappings between an orientation measured by the inertial sensors, the measured physiological parameters and an action to be performed as result of the identified gesture, is stored in the memory 108. At operation 704, the orientation calibrator 106 dynamically performs an action based on the orientation model 114 stored in the memory 108. At operation 706, the orientation calibrator 106 further detects if there is any change in the signal detected. If a change is detected then, at operation 708, the orientation calibrator 106 modifies the physiological parameter based on the change in the physiological parameter. At operation 710, the absolute orientation of the wearable device 100 is determined by the orientation calibrator 106 based on the stored mapping and the modified physiological parameter. At operation 712, the orientation calibrator 106 causes the wearable device 100 to dynamically perform an action based on the determined orientation.

Figure 8:
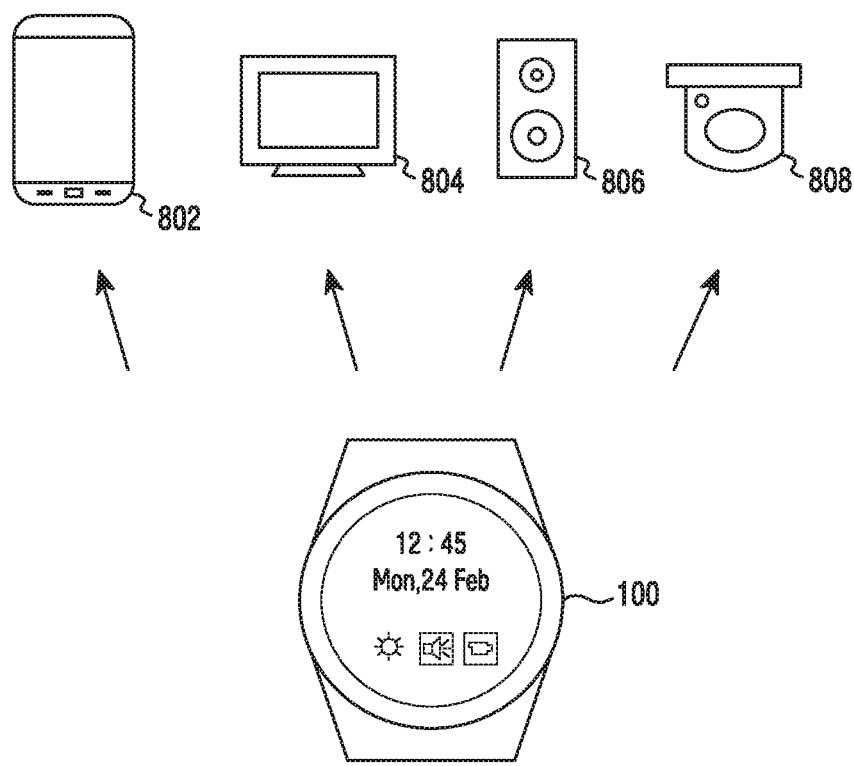
FIG. 8 illustrates an example scenario in which the wearable device can be used to control other devices using gestures, according to an embodiment of the disclosure.
Figure 9:
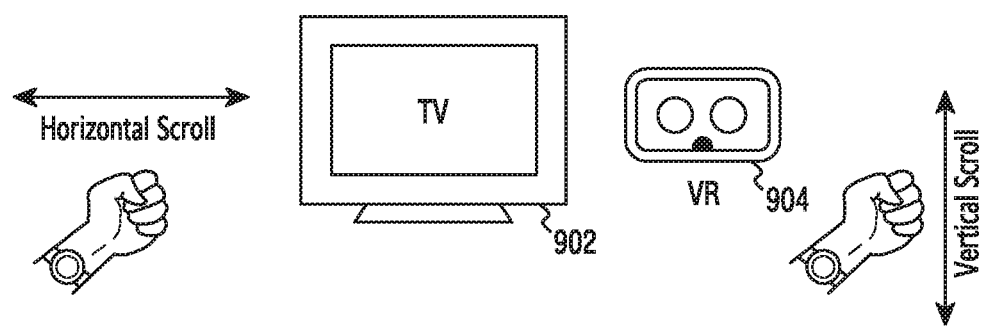
FIG. 9 illustrates an example scenario in which the wearable device can be used to control a television and a virtual reality (VR) devices using gestures, according to an embodiment of the disclosure.

FIGS. 8 and 9 illustrate various applications where the wearable device 100 can be used to control other devices using gestures, according to various embodiments of the disclosure.

Referring to FIG. 8, the wearable device 100 can act as a controller to point-and-connect to a tablet computer 802, a TV 804, a sound system 806 and a VR device 808. If the wearable device 100 is connected to an IoT network, then the wearable device 100 can be used to control any IoT device. Further, any arm gesture can then be performed by the user to control the IoT device.

FIG. 9 illustrates gestures that can be used to control the operation of a television 902 and a VR device 904. A horizontal scroll by the user with the wearable device 100 can scroll through a menu on the display screen of the television 902. The wearable device 100 detects the horizontal gesture by determining the absolute orientation and in accordance with the mapping in the orientation model 114, performs the action of scrolling through a menu on the display screen. Similarly, a vertical scroll by the user with the wearable device 100 may be equivalent to an action in a VR application executed by the VR device 904.

Figure 10:
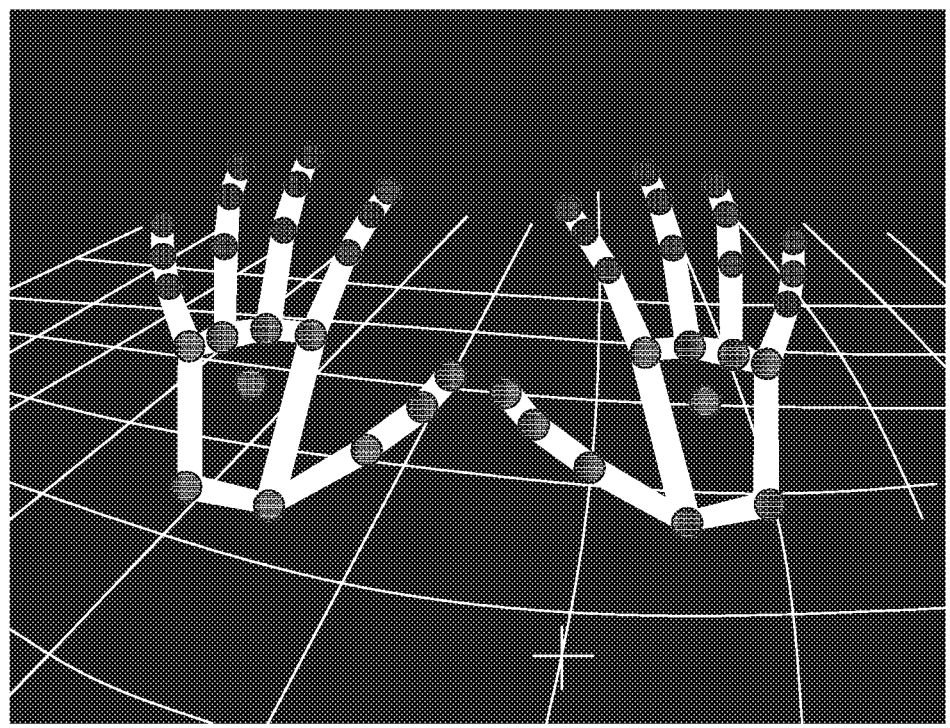
FIG. 10 illustrates a finger orientation tracking in a VR application, according to an embodiment of the disclosure.

FIG. 10 illustrates a finger orientation tracking in a virtual reality (VR) application, according to an embodiment of the disclosure.

Referring to FIG. 10, the wearable device 100 can potentially track wrist orientation and finger joint orientation. The wearable device 100 can track multiple joints instead of multiple rings. A single wrist device can track multiple fingers. The wearable device 100 can track static hand poses using the sensors 102. It can also track dynamic gestures using the inertial sensor. Knowing the configuration of the user's fingers/wrist, it can be mapped to the extent of force applied in the VR application.

Figure 11:
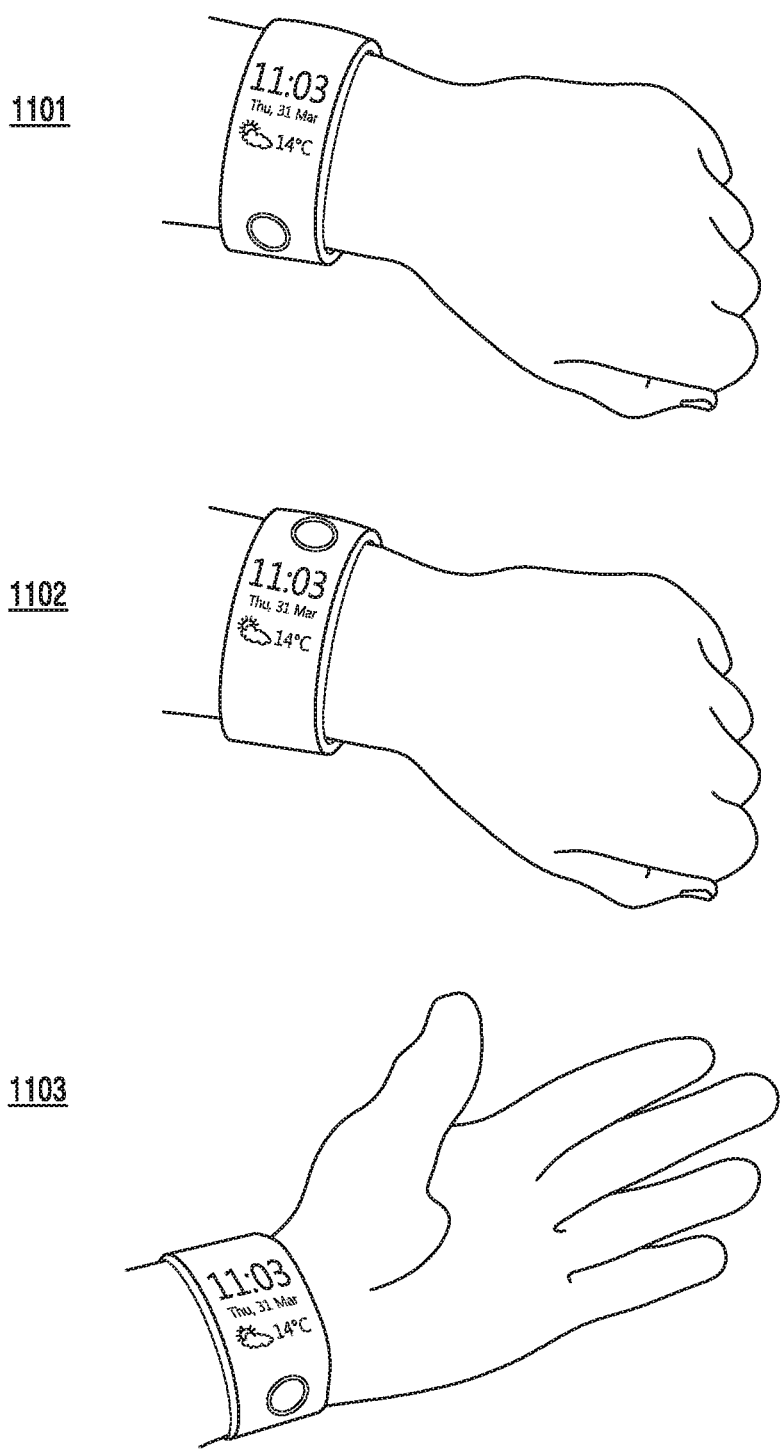
FIG. 11 illustrates an example of a situation in which a screen is displayed in accordance with the orientation of the wearable device, according to an embodiment of the disclosure.

FIG. 11 illustrates an example of a situation in which a screen is displayed in accordance with the orientation of the wearable device according to an embodiment of the disclosure. The wearable devices shown in FIG. 11 may correspond to the wearable device 100.

Referring to FIG. 11, the wearable device 100 may be configured as an all round display (e.g., bangle type). The wearable device 100 can change an area for displaying the screen in accordance with the detected orientation of the wearable device 100. For example, the wearable device 100 may further include at least one of a gravity sensor, a gyro sensor, or an acceleration sensor (not shown). The wearable device can estimate (or predict) the direction of the user's gaze using at least one of the gravity sensor, the gyro sensor, the acceleration sensor, or the array of the body sensors (or biometric sensors). In some embodiments, the wearable device may further include an image sensor (not shown). For example, the wearable device can perform eye tracking or face detection using the image sensor. The wearable device may display a screen on an area facing the user's eyes (or face) based on the eye tracking or the face detection.

The wearable device can distinguish the situations 1101, 1102, and 1103, and can display a screen at different positions according to the situations 1101, 1102, and 1103.

Figure 12:
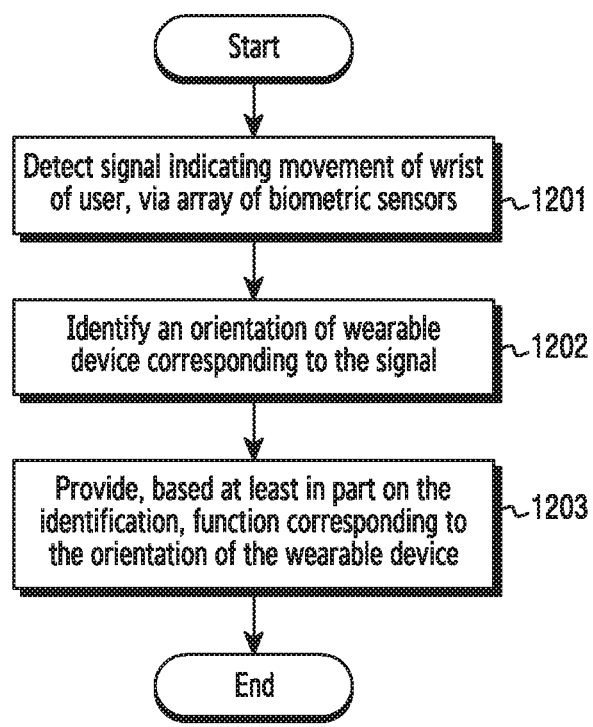
FIG. 12 is a flow diagram illustrating a method of performing actions by the wearable device, according to an embodiment of the disclosure.

FIG. 12 is a flow diagram illustrating a method of performing actions by the wearable device, according to an embodiment of the disclosure.

Referring to FIG. 12, The operations described in FIG. 12 can be performed by the wearable device 100. The wearable device is capable of being worn on a wrist of a user. The wearable device may comprise a substantially circular band having an inner peripheral surface and an outer peripheral surface, an array of biometric sensors (e.g., sensors 102) exposed through the inner peripheral surface, and at least one processor (e.g., processor 110).

Referring to FIG. 12, in operation 1201, the processor 110 may detect at least one signal indicating a movement of a muscle of the wrist, via the array of the biometric sensors. In operation 1202, the processor 110 may identify an orientation of the wearable device corresponding to the at least one signal. For example, the orientation of the wearable device may indicate a wearing position of the band. In operation 1203, the processor 110 may provide, based at least in part on the identification, a function corresponding to the orientation of the wearable device.

The embodiments disclosed herein can be implemented through at least one software program running on at least one hardware device and performing network management functions to control the elements. The elements shown in FIGS. 1A-1C include blocks which can be at least one of a hardware device, or a combination of hardware device and software module.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A wearable device capable of being worn on a wrist of a user, the wearable device comprising:
   a substantially circular band having an inner peripheral surface and an outer peripheral surface;
   an array of biometric sensors exposed through the inner peripheral surface; and
   at least one processor configured to:
   detect at least one signal indicating a movement of a muscle of the wrist, via the array of the biometric sensors,
   identify an orientation of the wearable device corresponding to the at least one signal based on a pre-stored mapping, and
   provide, based at least in part on the identification, a function corresponding to the orientation of the wearable device,
   wherein the pre-stored mapping indicates correspondence between signals indicating movements of the muscle of the wrist and orientations of the wearable device.

2. The wearable device of claim 1 wherein the at least one processor is further configured to:
   in response to detecting that a gesture is performed by the user, detect the at least one signal.

3. The wearable device of claim 1, wherein the at least one processor is further configured to:
   measure at least one physiological parameter from the at least one detected signal;
   detect an absolute orientation of the wearable device using at least one of an inertial sensor or the array of biometric sensors; and
   dynamically perform an action based on a pre-stored mapping of the at least one physiological parameter and the absolute orientation of the wearable device.

4. The wearable device of claim 3, wherein the at least one physiological parameter is represented as one or more images indicative of an impedance map.

5. The wearable device of claim 3, wherein the at least one physiological parameter is indicative of at least one of muscle activity of the user, finger movement performed by the user, a wrist contour of the user, a force applied through a gesture by the user, a force applied on the wearable device by the user, a pulse rate of the user, an electrical activity produced by muscles of the user, changes in volume of an artery or a vein of the user or a cross-sectional impedance across the array of biometric sensors.

6. The wearable device of claim 3, wherein the at least one processor is further configured to:
   detect a change in the at least one signal using at least one of the inertial sensor and the array of biometric sensors,
   modify the at least one physiological parameter based on the change in the at least one signal,
   determine the absolute orientation of the wearable device based on the pre-stored mapping and the at least one modified physiological parameter, and dynamically perform an action based on the determined absolute orientation.

7. The wearable device of claim 1, wherein the at least one processor is further configured to:
identify a finger movement performed by the user by analyzing the movement of the muscle of the wrist, and
provide a function corresponding to the finger movement in consideration of the orientation of the wearable device.

8. The wearable device of claim 1, wherein the at least one processor is further configured to:
identify a wearing position of the substantially circular band by analyzing the at least one detected signal,
identify a gesture of a hand in consideration of the wearing position, and
perform a function corresponding to the gesture of the hand.

9. The wearable device of claim 1, wherein the at least one processor is further configured to:
identify the orientation of the wearable device using a machine learning based model stored in a memory of the wearable device.

10. The wearable device of claim 9, wherein the at least one processor is further configured to:
modify the model based on detecting a change of the orientation of the wearable device.

11. A method for performing actions by a wearable device capable of being worn on a wrist of a user, the method comprising:
detecting at least one signal indicating a movement of a muscle of the wrist, via an array of biometric sensors exposed through an inner peripheral surface of a substantially circular band of the wearable device;
identifying an orientation of the wearable device corresponding to the at least one signal based on a pre-stored mapping; and
providing, based at least in part on the identification, a function corresponding to the orientation of the wearable device,
wherein the pre-stored mapping indicates correspondence between signals indicating movements of the muscle of the wrist and orientations of the wearable device.

12. The method of claim 11, wherein the detecting of the at least one signal comprises:
in response to detecting that a gesture is performed by the user, detecting the at least one signal.

13. The method of claim 11, wherein the identifying of the orientation of the wearable device comprises:
measuring at least one physiological parameter from the at least one detected signal,
detecting, by the wearable device, an absolute orientation of the wearable device using at least one of an inertial sensor or the array of biometric sensors, and
dynamically performing an action, by the wearable device, based on a pre-stored mapping of the at least one physiological parameter and the absolute orientation of the wearable device.

14. The method of claim 13 wherein the at least one physiological parameter is represented as one or more images indicative of an impedance map.

15. The method of claim 13, wherein the at least one physiological parameter is indicative of at least one of muscle activity of the user, finger movement performed by the user, a wrist contour of the user, a force applied through a gesture by the user, a force applied on the wearable device by the user, a pulse rate of the user, an electrical activity produced by muscles of the user, changes in volume of an artery or a vein of the user or a cross-sectional impedance across the array of biometric sensors.

16. The method of claim 13, further comprising:
detecting, by the wearable device, a change in the at least one signal, using at least one of an inertial sensor or the array of biometric sensors;
modifying, by the wearable device, the at least one physiological parameter based on the change in the at least one signal;
determining, by the wearable device, an absolute orientation of the wearable device based on the pre-stored mapping and the at least one modified physiological parameter; and
dynamically performing, by the wearable device, an action based on the determined absolute orientation.

17. The method of claim 11, wherein the providing of the function based at least in part on the identification comprises:
identifying a finger movement performed by the user by analyzing the movement of the muscle of the wrist, and
providing the function corresponding to the finger movement in consideration of the orientation of the wearable device.

18. The method of claim 11, wherein the providing of the function based at least in part on the identification comprises:
identifying a wearing position of the substantially circular band by analyzing the at least one detected signal,
identifying a gesture of a hand in consideration of the wearing position, and
performing a function corresponding to the gesture of the hand.

19. The method of claim 11, wherein the identifying of the orientation of the wearable device comprises:
identifying the orientation of the wearable device using a machine learning based model stored in a memory of the wearable device.

20. The method of claim 19, further comprising:
modifying the model based on detecting a change of the orientation of the wearable device.

* * * * *